(12) United States Patent
Ngowe et al.

(10) Patent No.: US 6,649,793 B1
(45) Date of Patent: Nov. 18, 2003

(54) PROCESS FOR THE PREPARATION OF A N, N-DIAMINO AMINO ACID-β-HYDROXY DISUCCINIC ACID

(75) Inventors: Charles Ngowe, Lansing, MI (US); Kris A. Berglund, Okemos, MI (US)

(73) Assignees: Board of Trustees of Michigan State University, East Lansing, MI (US); Applied CarboChemicals, Alto, MI (US)

(*) Notice: Subject to any disclaimer, the term of this patent is extended or adjusted under 35 U.S.C. 154(b) by 0 days.

(21) Appl. No.: 10/152,141

(22) Filed: May 21, 2002

(51) Int. Cl.$^7$ ............................................. C07C 229/00
(52) U.S. Cl. ................................................ 562/565
(58) Field of Search .......................................... 562/565

(56) References Cited

U.S. PATENT DOCUMENTS

| | | | | |
|---|---|---|---|---|
| 3,637,511 A | * | 1/1972 | Yang ........................... | 252/137 |
| 3,929,874 A | * | 12/1975 | Beermann et al. ........... | 252/534 |
| 5,183,590 A | * | 2/1993 | Carter et al. ................ | 252/392 |
| 5,318,726 A | * | 6/1994 | Rossmaier et al. ......... | 252/546 |
| 5,362,412 A | * | 11/1994 | Hartman et al. ............. | 252/94 |
| 5,905,160 A | | 5/1999 | Shimomura et al. | |

FOREIGN PATENT DOCUMENTS

JP        8067659 A      3/1996

OTHER PUBLICATIONS

Stecher et al, The Merck Index, Nov. 1975, Merck & Co., Inc . 8$^{th}$ ed. , p. 738.*
McManus, P.S., et al., Synthetic Comm. 3, 177 (1973).
Rechnitz, G.A., et al., Anal. Chem. 40 696 (1968).
Nagarajan, M.K., et al., JAOCS 61 1475 (1984).
Blay, J.A., et al., Anal. Lett. 4, 653 (1971).

* cited by examiner

*Primary Examiner*—Alan L. Rotman
*Assistant Examiner*—Taylor V Oh
(74) *Attorney, Agent, or Firm*—Ian C. McLeod

(57) ABSTRACT

A process of the preparation of a N,N-diamino amino acid-β-hydroxy-succinic acid as a N,N-diacid salt (I) is described. The process involves reacting epoxy succinic acid with an amino acid having two amino groups as an N-acid salt. The compounds are useful as chelators.

6 Claims, 1 Drawing Sheet

PROCESS FOR THE PREPARATION OF A N, N-DIAMINO AMINO ACID-β-HYDROXY DISUCCINIC ACID

BACKGROUND OF THE INVENTION

(1) Field of the Invention

The present invention relates to a process for the preparation of a 2N, 6N-diamino-amino acid-β-hydroxy disuccinic acid, as a N,N-diacid salt, in particular 2N, 6N-dilysine-β-hydroxy disuccinic acid as a N,N-dihydrochloride salt. Any of the compounds can be converted to an alkali metal salt from (Na, K). The process involves reaction of a diamino acid as an acid salt with epoxy succinic acid. The amino acids can be in D or L isomers and the epoxy succinic acid can be in a cis- or trans-form.

(2) Description of Related Art

Japanese Patent No. 8067659A describes a basic reaction of lysine or its potassium or ammonium salts and an epoxy amino acid or its salts under neutral or basic conditions to produce lysine disuccinic acid compounds which are useful as chelators. The lysine is as the free amine. The process requires acidulation of the reaction mixture to form an acid salt which is separated as an additional step.

The preparation of epoxy succinic acid is described in U.S. Pat. No. 5,905,160 to Shimomura et al. An ethylamine compound is epoxidated with hydrogen peroxide.

There is a need for an improved process for the preparation of the disuccinic acid derivatives.

OBJECTS

It is therefore an object of the present invention to provide an improved process for the preparation of the succinic acid derivatives. It is further an object of the present invention to provide a process which is relatively easy to perform and which is economical.

SUMMARY OF THE INVENTION

The present invention relates to a process for the preparation of a N,N-diamino-amino acid-β-hydroxy disuccinic acid (I) as a N,N diacid salt which comprises: reacting an N-acid salt of an N,N-diamino-amino acid with epoxy succinic acid in a solvent; and separating (I) from the reaction mixture. The preferred amino acid is lysine. The process is preferably conducted in an aqueous solution as the solvent heated to less than 100° C., in the absence or presence of oxygen. The reaction is most preferably conducted under a nitrogen atmosphere. The separation is preferably conducted by adding ethanol and/or the methanol to the solution which is removed with the aqueous solution, and wherein I is washed with ethanol and solvent to purified I.

The process produces a N,N-diamino-amino acid-β-hydroxy disuccinic acid as an N,N-diacid salt and in particular 2N,6N-lysine-β-hydroxy disuccinic acid as a N,N-dihydrochloride salt. The preferred compound has the formula (II)

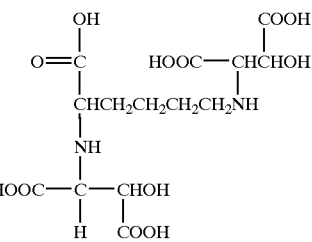

The acids used can be any mineral or organic acid which forms a salt with the amino acid. Most commonly an inorganic acid such as hydrochloric acid is used for cost reasons, although sulfuric acid can be used.

The amino acids can be asparagine, glutamine, tryptophan, argenine, histidine and lysine, which are preferred for reasons of cost.

DESCRIPTION OF PREFERRED EMBODIMENTS

The following is a specific description of the synthesis of a lysine amino acid β-hydroxy disuccinic acid as a hydrochloride salt (II) under acidic conditions. The compound is useful as a chelator with high water solubility and improved biodegradability.

The present invention relates to a novel process for preparing compound (II) under acidic conditions. The amino acid sequesterant builder compounds of the prior art (Japanese Patent No. JP8067659A) is carried out under substantially neutral to mildly basic conditions (Japanese Patent No. JP8067659A). In the present invention, the compound I derivative corresponding to scheme (1) are prepared by reaction of lysine hydrochloride with epoxy succinic acid, preferably in molar ratios of 1:2 to 2.5.

Scheme I

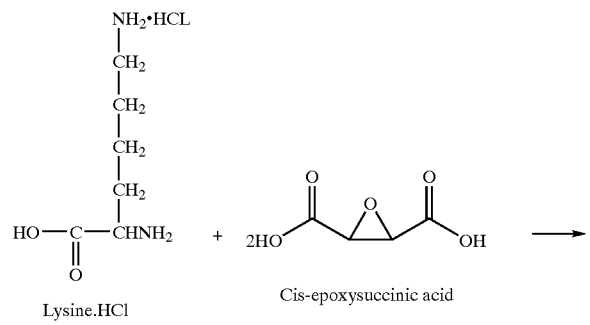

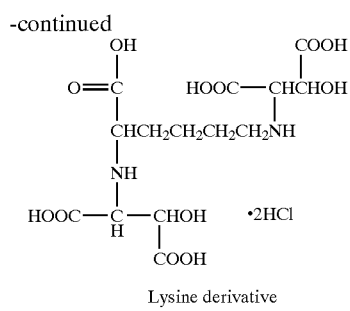

Lysine derivative

The reaction is carried out under substantially acidic conditions, preferably in the presence of lysine monohydrochloric acid or lysine dihydrochloric acid as a starting compound. The product has one mole of lysine for each two moles of succinic acid. The product yield is as high as 90–100% depending strictly on reaction time. In one particularly preferred embodiment of the production process, a molar ratio of 1:2 of the mono, or dihydrochloride amino acid salts and epoxy succinic acids are used as starting compunds. The reaction mixture is allowed to react in aqueous medium at ambient temperature or 40–150° C. Ethanol is added into the solution until two immiscible liquids form. The top liquid ethanol/water azeotrope is decanted off and the remaining filtrate is repeatedly washed with ethanol followed by acetone to remove unreacted epoxy succinic acid.

In the context of the invention, "epoxy succinic acid" is used as a synonym both for cis- and for trans-epoxy succinic acid and for mixtures thereof; the trans form may be present as one of the enantiomers or as a mixture of both, for example as racemate. Similarly, "N-acid salt" stands both for the L- and for D-lysine N-acid salt and also for mixtures thereof, for example the racemate. For other amino acids, they are also N-acid salts.

EXAMPLE 1

Synthesis of Compound (II)

Figure 1:
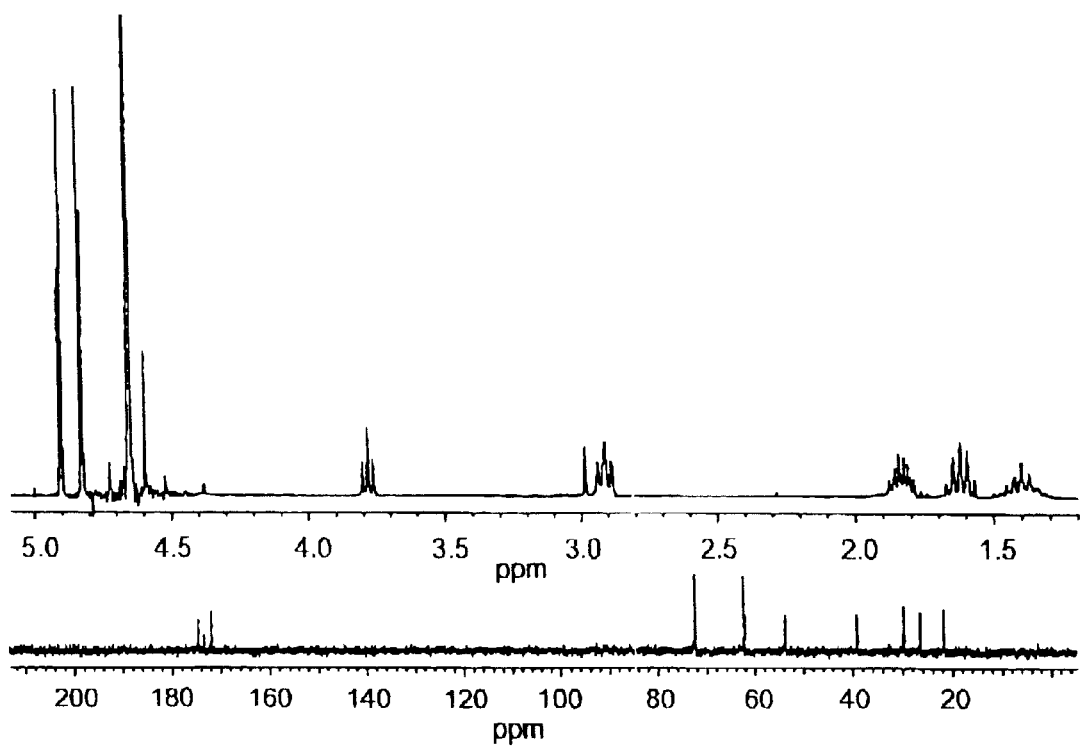
FIG. 1 is a graph showing NMR data of the lysine derivative.

To 5 mL of deionized water containing 5.0034 grows (0.03788 mols) of cis-epoxysuccinic acid was added 4.1502g (0.01894 mols) of L-Lysine dihydrochloride (McManus, P. S., et al., *Synthetic Comm.* 3, 177 (1973)). The reaction mixture was refluxed at 80° C. for 4 hours under a nitrogen atmosphere, then allowed to cool to room temperature. Ethanol was added into the solution until two immiscible liquids formed. The top liquid ethanol/water azeotrope is decanted off and the remaining filtrate was repeatedly washed-with ethanol followed by acetone to remove unreacted epoxy succinic acid. The product was characterized by $^1$H NMR, and $^{13}$C NMR, as shown in FIG. 1. The NMR was recorded using a 300-MHz Varian INOVA spectrometer.

EXAMPLE 2

Calibration Curve

Calcium chloride dihydrate was purchased from Fisher Scientific. A stock solution of 0.01M $CaCl_2.2HCl$ (1000 ppm, hardness $CaCO_3$) was prepared with distilled deionized water, and 0.03M $NH_4Cl/0.07M$ $NH_4OH$ buffer (pH= 9.5, ionic strength of 0.1M). The later chemicals were obtained from Columbus Chemical Industries, Inc. Standard solution ranging from 200 ppm to 10 ppm was prepared by dilution of the stock solution with the buffer. A plot of the logarithm of calcium ion concentration vs the normalized potential was constructed prior to each titration (Rechnitz, G. A., et al., *Anal. Chem.* 40 696 (1968); and Nagarajan, M. K., et al., *JAOCS* 61 1475 (1984)). This was necessary to minimize the effect of signal fluctuations due to solution condition (ionic strength, pH, and the like). Potentiometric measurements were conducted with calcium-selective electrode obtained from Orion Research, Inc. (model 97-20 ionplus electrode).

EXAMPLE 3

Titration

Figure 2:
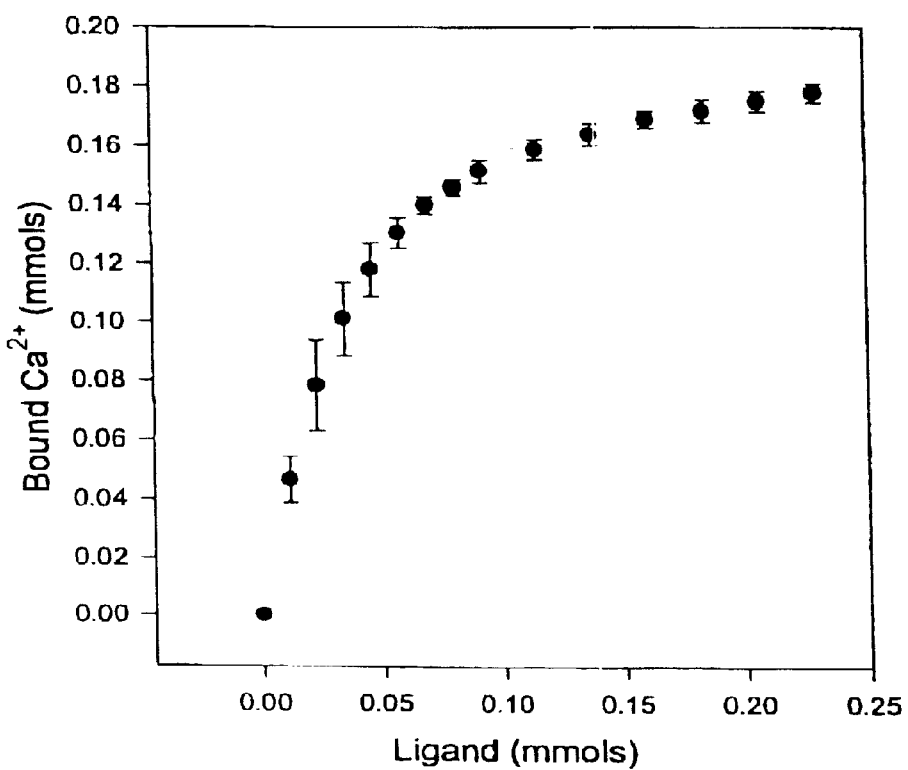
FIG. 2 is a graph of moles of bound $Ca^{2+}$ vs moles of titrant (N,N succinol lysine). The data of bound calcium was from the average of three replicates.

The electrode was immersed in a 50 mL of 200 ppm hardness solution at 25° C., and the meter reading was taken while the solution was being stirred by magnet (Blay, J. A., et al., *Anal. Lett.* 4, 653 (1971)). The calcium binding solution of Compound II was added in small increments and the equilibrium-free calcium ion concentration were measured. When the meter reading indicated less than 10 ppm present in solution, the titration was stopped. The data collected was normalized, and from the calibration curve the concentration of the free calcium ion was obtained. FIG. 2 shows that the bound calcium increased as a function of compound II added. At low concentration of added compound II, there is a linear relationship between added chelating agent and amount of calcium bound. Chelation constant (logK) of compound II was determined to be 4.23±0.09 according to the following equation $$K = \frac{[Ca_2L^{(n-2)^-}]}{[Ca^{2+}]^2[L^{n-}]}$$

where L represents the chelating agent and n is the anionic charge on the chelator.

It is intended that the foregoing description be only illustrative of the present invention and that the present invention be limited only by the hereinafter appended claims.

We claim:

1. A process for the preparation of a N,N-diamino-amino acid-β-hydroxy disuccinic acid (I) which comprises:
   (a) reacting an N-acid salt of an N,N-diamino-amino acid with epoxy succinic acid in an aqueous solvent under substantially acidic conditions to produce (I); and
   (b) separating (I) from the reaction mixture.

2. The process of claim 1 wherein the amino acid is lysine.

3. The process of claim 1 conducted in water as the aqueous solvent which is heated to less than 100° C.

4. The process of any one of claims 1, 2 or 3 wherein the reaction of step (a) is conducted under a nitrogen atmosphere.

5. The process of claims 1, 2 or 3 wherein the separation is by adding ethanol to the aqueous solvent which is removed with the aqueous solvent and wherein I is washed with ethanol as a solvent to produce purified I.

6. A process for the preparation of a 2N,6N-lysine-β-hydroxy disuccinic acid which comprises:
   (a) reacting an N-acid salt of lysine with epoxy succinic acid in an aqueous solvent under substantially acidic conditions to produce the 2N,6N-lysine-β-hydroxy disuccinic acid; and
   (b) separating the 2N,6N-lysine-β-hydroxy disuccinic acid from the reaction mixture.

* * * * *